United States Patent [19]

Tang

[11] Patent Number: 4,473,648

[45] Date of Patent: Sep. 25, 1984

[54] PROCESS AND NUTRIENT MEDIUM FOR MICROPROPAGATION OF CASSAVA

[75] Inventor: Archie F. Tang, Redwood City, Calif.

[73] Assignee: International Plant Research Institute, San Carlos, Calif.

[21] Appl. No.: 378,420

[22] Filed: May 14, 1982

[51] Int. Cl.³ .......................... C12N 5/00; C12R 1/91; A01G 1/00

[52] U.S. Cl. .................................. 435/240; 435/948; 47/58

[58] Field of Search ...................... 435/240, 948; 47/58

[56] References Cited

U.S. PATENT DOCUMENTS 4,003,156  1/1977  Sibi et al. ................................. 47/58

OTHER PUBLICATIONS

Murashige, "Plant Tissue Culture and its Importance to Agriculture" in, Practical Tissue Culture Applications, ed. Maramorosch et al., (1979), pp. 27–31.
Murashige, "Sample Preparations of Media" in, Tissue Culture, Methods and Applications, ed., Kruse et al., (1973), pp. 698–702.
Narayanaswamy, "Regeneration of Plants from Tissue Cultures" in, Plant Cell, Tissue, and Organ Culture, ed. Reinert et al., (1977), pp. 179–195.
Shahin et al, "Cassava Mesophyll Protoplasts: Isolation, Proliferation and Shoot Formation," Plant Science Letters 17, pp. 459–465, (1980).
Kartha et al, "Regeneration of Cassava Plants from Apical Meristems", Plant Science Letters 2, pp. 107–113, (1974).
Prabhudesai et al, "A Tissue Culture from Tapioca", Plant Science Letters 4, pp. 237–241, (1975).
Parke, "Tissue Culture of Cassava on Chemically Defined Medium" Physioligua Plantarum 42(2), pp. 195–201, (1978).
Kaiser et al, "Use of Tissue Culture and Thermotherapy to Free East African Cassava Cultivars of African Cassava Mosaic", Plant Disease Reporter 63(9), pp. 780–784, (1979).

Primary Examiner—Thomas Wiseman
Assistant Examiner—John E. Tarcza
Attorney, Agent, or Firm—John P. White

[57] ABSTRACT

A medium is provided which is useful in a fast and convenient system for multiplying cassava plants vegetatively by means of in vitro micropropagation of nodal cultures. This medium includes in parts per million the following:

| | |
|---|---|
| about 1200 | $NH_4NO_3$ |
| from about 1000–1500 | $KNO_3$ |
| about 300 | $MgSO_4.7H_2O$ |
| from about 150–300 | $NaH_2PO_4.H_2O$ |
| from about 150–300 | $CaCl_2.2H_2O$ |
| from about 18.5–37 | $Na_2.EDTA$ |
| from about 13.9–27.8 | $FeSO_4.7H_2O$. | and suitable amounts of essential ingredients for a cassava micropropagation medium.

In paticular, the medium also contains in part per million about: 3.0 $H_3BO_3$, 10.0 $MnSO_4.H_2O$, 6.0 $ZnSO_4.7H_2O$, 0.25 $Na_2MoO_4.2H_2O$, 0.025 $CuSO_4.5H_2O$, 0.025 $CaCl_2.6H_2O$, 0.75 KI, 2.5 Nicotinic acid, 10.0 Thiamine HCl, 1.0 Pyridoxine HCl, 100.0 M-inositol, 0.5 Glycine, 0.5 Folic acid, 0.05 Biotin, 0.5 D-Ca-Pantothenate, 0.25 Riboflavin, 0.5 Ascorbic acid, 0.1 choline chloride, 1.0 L-cysteine HCl, 10.0 Malic acid and 50.0 Casein Hydrolysate. Furthermore, the medium desirably contains about 3 percent sucrose or glucose.

4 Claims, No Drawings

PROCESS AND NUTRIENT MEDIUM FOR MICROPROPAGATION OF CASSAVA

BACKGROUND OF THE INVENTION

Cassava is a major crop in numerous developing countries, where it is used as a food source for both humans and animals. In addition, cassava contains a high concentration of starch which can be converted into alcohol, syrup or glue. A protoplast regeneration system for cassava could be of considerable value in efforts to improve this important plant through genetic modification. Previously, cassava plants have been regenerated from meristem culture [Berbee, F. M. et al., In Vitro, Annual Meetings (1974), 421 (Abstr.) and Kartha, K. K., et al., Plant Sci. Lett. 2 (1974) 107]; stem callus [Tilguin, J. P., Can J. Bot. 57 (1979) 1761]; protoplast cultures [Shahin, E. A. and Shepard, J. F., Plant Science Letters 17 (1980) 459–465] and somatic embryogenesis [Stamp, J. A. and Henshaw, G. G. Z. Pflanzen Physiol. Bd. 105 (1982) 183–187].

In order to pursue efforts intended to improve the genetic make-up of cassava, it would be desirable to have a fast and convenient system for multiplying cassava plants vegetatively by means of in vitro micropropagation techniques. To this end, a number of media have been prepared and compared, certain of which provide distinct advantages over previously known media.

SUMMARY OF THE INVENTION

A medium for in vitro micropropagation of cassava includes in parts per million the following:

| | |
|---|---|
| about 1200 | $NH_4NO_3$ |
| from about 1000–1500 | $KNO_3$ |
| about 300 | $MgSO_4.7H_2O$ |
| from about 150–300 | $NaH_2PO_4.H_2O$ |
| from about 150–300 | $CaCl_2.2H_2O$ |
| from about 18.5–37 | $Na_2.EDTA$ |
| from about 13.9–27.8 | $FeSO_4.7H_2O$ | and suitable amounts of essential ingredients for a cassava micropropagation medium.

Specifically, essential ingredients and suitable amounts thereof in parts per million are as follows: 3.0 $H_3BO_3$, 10.0 $MnSO_4.H_2O$, 6.0 $ZnSO_4.7H_2O$, 0.25 $Na_2MoO_4.2H_2O$, 0.025 $CuSO_4.5H_2O$, 0.025 $CaCl_2.6H_2O$, 0.75 KI, 2.5 Nicotinic acid, 10.0 Thiamine HCl, 1.0 Pyridoxine HCl, 100.0 M-inositol, 0.5 Glycine, 0.5 Folic acid, 0.05 Biotin, 0.5 D-Ca-Pantothenate, 0.25 Riboflavin, 0.5 Ascorbic acid, 0.1 Choline chloride, 1.0 L-cysteine HCl, 10.0 Malic acid and 50.0 Casein Hydrolysate. Furthermore, the medium desirably contains about 3 percent sucrose or glucose.

Cultivation of nodal cultures under suitable conditions on such a medium provides a method for in vitro micropropagation of cassava.

DETAILED DESCRIPTION OF THE INVENTION

Cassava stems with apical or auxillary buds, but no leaves or petioles were recovered from the following cultivars: Senoreta, MCOL 1684, MPAN 12-A, MCOL 22, MPAN 19, CM 489-1, MCOL 1940, CMC 92, Secundina, MCOP 647, MVEN 48, CM 321-188, MMEX 59, MCOL 1467, MVEN 28, MCOL 638X CM 516-6, Cano, Cenape, Tacuara, Pyta, San Quintin, Tabai, MVEN 218, MCOL 1468, HMC-2, CM 305-41, CM 308-197, MCOL 1513, CM 91-3, CM 342-55, CM 323-375, Fowl Fat, MCOL 1488, CM 507-34, CM 507-37, Pombero Grande de la Zona de 'El Colorado', Taqueri S-2901, CM 391-2, O'Hair, S 18-7, MCOL 1438, Cerro Azul 10-4, Cerro Azul 8-14, Verde Olivo, Pombero Grande Procedencia "Paraguay", Cerro Azul 3-4, San Rafael and Cerro Azul SN6.

The surfaces of the stems were sterilized by soaking in 10 percent Chlorox for 10 to 20 minutes, then in 70 percent alcohol for 20 to 30 seconds, followed by rinsing 3 or 4 times in sterile deionized water.

Cuttings involved one node per section. The stem sections were cultured by inserting them in medium with the buds right side up. The cultures were incubated under 3000–5000 lux light 8 hours dark, at 27°–30° C. In evaluating growth it was considered normal if shoots started budding out in 2–3 days and roots started developing in 4–7 days. Subcuttings or sub-cultures can be made in 3–4 weeks when the node develops into a plantlet about 4–5 inches high with 4-5 nodes.

The compositions of the cassava culture medium bases examined are shown in Table I.

TABLE I

Compositions of Cassava Cultural Medium Bases

| Ingredient (ppm) | MS | $B_5$ | $C_1$ | $C_2$ | $C_3$ | $C_4$ | $C_{11}$ | $C_{16}$ |
|---|---|---|---|---|---|---|---|---|
| $NH_4NO_3$ | 1,650 | — | 1,200 | 1,200 | 1,200 | 1,200 | 1,200 | 600 |
| $KNO_3$ | 1,900 | 2,500 | 1,000 | 1,000 | 1,500 | 1,500 | 1,500 | 1,500 |
| $MgSO_4.7H_2$ | 370 | 250 | 300 | 300 | 300 | 300 | 300 | 300 |
| $KH_2PO_4$ | 170 | — | — | — | — | — | — | — |
| $NaH_2PO_4.H_2O$ | — | 150 | 150 | 300 | 150 | 150 | 300 | 150 |
| $CaCl_2.2H_2O$ | 435 | 150 | 150 | 150 | 150 | 300 | 600 | 150 |
| Ferric Versenate | 40 | 28 | — | — | — | — | — | — |
| $Na_2.EDTA$ | — | — | 18.5 | 18.5 | 18.5 | 37.0 | 37.0 | 18.5 |
| $FeSO_4.7H_2O$ | — | — | 13.9 | 13.9 | 13.9 | 27.8 | 27.8 | 13.9 |
| $(NH_4)_2SO_4$ | — | 134 | — | — | — | — | — | — |
| $H_3BO_3$ | 6.2 | 3.0 | 3.0 | 3.0 | 3.0 | 3.0 | 6.0 | 3.0 |
| $MnSO_4.H_2O$ | 22.3 | 10.0 | 10.0 | 10.0 | 10.0 | 10.0 | 20.0 | 10.0 |
| $ZnSO_4.7H_2O$ | 8.6 | 2.0 | 6.0 | 6.0 | 6.0 | 6.0 | 0.9 | 6.0 |
| $Na_2MoO_4.2H_2O$ | 0.25 | 0.25 | 0.25 | 0.25 | 0.25 | 0.25 | 0.25 | 0.25 |
| $CuSO_4.5H_2O$ | 0.025 | 0.025 | 0.025 | 0.025 | 0.025 | 0.025 | 0.025 | 0.025 |
| $CoCl_2.6H_2O$ | 0.025 | 0.025 | 0.025 | 0.025 | 0.025 | 0.025 | 0.025 | 0.025 |
| KI | 0.75 | 0.75 | 0.75 | 0.75 | 0.75 | 0.75 | 0.75 | 0.75 |
| Nicotinic acid | 1.0 | 1.0 | 2.5 | 2.5 | 2.5 | 2.5 | 2.5 | 2.5 |
| Thiamine | 10.0 | 10.0 | 10.0 | 10.0 | 10.0 | 10.0 | 10.0 | 10.0 |

TABLE I-continued

Compositions of Cassava Culture Medium Bases

| (ppm) Ingredient | MS | B$_5$ | C$_1$ | C$_2$ | C$_3$ | C$_4$ | C$_{11}$ | C$_{16}$ |
|---|---|---|---|---|---|---|---|---|
| Pyridoxine HCL | 1.0 | 1.0 | 1.0 | 1.0 | 1.0 | 1.0 | 1.0 | 1.0 |
| M—inositol | 100.0 | 100.0 | 100.0 | 100.0 | 100.0 | 100.0 | 100.0 | 100.0 |
| Glycine | — | — | 0.5 | 0.5 | 0.5 | 0.5 | 0.5 | 0.5 |
| Folic acid | — | — | 0.5 | 0.5 | 0.5 | 0.5 | 0.5 | 0.5 |
| Biotin | — | — | 0.05 | 0.05 | 0.05 | 0.05 | 0.05 | 0.05 |
| D-Ca—Pantothenate | — | — | 0.5 | 0.5 | 0.5 | 0.5 | 0.5 | 0.5 |
| Riboflavin | — | — | 0.25 | 0.25 | 0.25 | 0.25 | 0.25 | 0.25 |
| Ascorbic acid | — | — | 0.5 | 0.5 | 0.5 | 0.5 | 0.5 | 0.5 |
| Choline Chloride | — | — | 0.1 | 0.1 | 0.1 | 0.1 | 0.1 | 0.1 |
| L-Cysteine HCL | — | — | 1.0 | 1.0 | 1.0 | 1.0 | 1.0 | 1.0 |
| Malic acid | — | — | 10.0 | 10.0 | 10.0 | 10.0 | 10.0 | 10.0 |
| Casein Hydrolysate | — | — | 50.0 | 50.0 | 50.0 | 50.0 | 50.0 | 50.0 |

These media, with or without phytohormone(s) and various types and concentrations of carbohydrates (Table 2), have been applied and compared.

TABLE 2

| Base* | Hormone(s) and Carbohydrate(s) |
|---|---|
| MS | (a) hormone-free (O-MS) |
| | (b) with 1.8% μM NAA and 0.44 μM BA (N-MS) |
| | (c) with 1.08% μM NAA, 0.44 μM BA and 0.15 μM GA (S-MS) containing 2%–5% sucrose. |
| B$_5$ | (a), (b) and (c) same as in MS as base (denoted as O-B$_5$, N-B$_5$, and S-B$_5$, respectively) |
| C$_1$ | (a), (b) and (c) same as in MS as base; and (d) with 0.1 ppm GA (denoted as O-C$_1$, N-C$_1$, S-C$_1$ and G-C$_1$, respectively) |
| C$_2$ | hormone-free, with 3% sucrose (O-C$_2$) |
| C$_3$ | hormone-free, with 3% sucrose or glucose (O-C$_3$) |
| C$_4$ | hormone-free, with 3% sucrose (O-C$_4$) |
| C$_{11}$ | hormone-free with 3% sucrose (O-C$_{11}$) |

*Ingredients and amounts shown in Table 1.

The results observed in terms of growth are shown in Table 3.

TABLE 3

| | Shoot Development* | | Root Development | |
|---|---|---|---|---|
| Medium | Speed | Nutritional Disorders | Speed | Callus Formation |
| O-MS | very slow | occasional | slow | none |
| N-MS | slow | occasional | slow | occasional |
| S-MS | slow | occasional | slow | occasional |
| O-B$_5$ | very slow | serious | slow | none |
| S-B$_5$ | slow | serious | slow | serious |
| N-B$_5$ | slow | serious | slow | serious |
| O-C$_1$ | fast | occasional | fast | none |
| N-C$_1$ | very slow | serious | slow | serious |
| S-C$_1$ | very slow | serious | slow | serious |
| G-C$_1$ | slow | occasional | slow | occasional |
| O-C$_2$ | fast | occasional | very fast | none |
| O-C$_3$ | very fast | occasional | very fast | none |
| O-C$_4$ | very fast | none | very fast | none |
| O-C$_{11}$ | slow | occasional | slow | occasional |

| | Development | | |
|---|---|---|---|
| Speed | Development Starts | 2 inch shoot | 4 inch shoot |
| very slow | more than 1 week | over 4 weeks | over 8 weeks |
| slow | ~1 week | ~4 weeks | ~8 weeks |
| fast | 4–5 days | ~2 weeks | ~4 weeks |
| very fast | 2–3 days | ~10 days | ~3 weeks |

*Descriptions

Nutritional ingredients in the traditional MS and B$_5$ media were found to be insufficient for cassava nodal cultures. Even if the nutrient deficiency symptoms do not show up in the first cuttings from potted plants, they will show up after 1 or 2 subcuttings in in vitro culture using the same ingredients.

The newly balanced C$_1$, C$_2$, C$_3$ and C$_4$ media, without the presence of growth regulators, have been tested very suitable for cassava nodal cultures. A single-noded stem segment can give rise to a 4–5 inches long, healthy looking plantlet with 4–5 new nodes ready for subcuttings in about one month. Furthermore, subcuttings cultured on the same media show even better results.

When the test-tube plants were transferred into pots, materials from MS and B$_5$ sources needed extra care and took a longer time to mature. On the other hand, plantlets growing in hormone-free C$_1$, C$_2$, C$_3$ and C$_4$ media (2-week-old to 3-month-old nodal cultures) grew faster in pots and appeared healthier. Furthermore, explants and tissues harvested from plantlets growing in hormone-free C$_1$, C$_2$, C$_3$ or C$_4$ media provided satisfactory results in meristem cultures and tissue cultures.

As the table shows, media C$_3$ and C$_4$, without the presence of hormones, provided particularly favorable results.

Isolation and culture of cassava mesophyll protoplasts originated from leaf material growing in vitro Young leaves of 3-week to 3-month old nodal cultures growing in hormone-free C$_3$ or C$_4$ media can be utilized.

Immediately before enzyme treatment of the leaves, the whole plantlets or the excised leaves preserved in a moisturized container were kept in the dark at room temperature for 24 to 72 hours. The dark treated leaves were then brushed on the lower epidermis to enhance the infiltration of the enzyme solution.

The enzymes pectinase or macerozyme, together with cellulase or cellulysin, at a ratio of 1 percent to 2 percent, respectively, were used. The basic part of the enzyme solution is C$_{16}$ media (for ingredients and amounts, see Table 1) with 0.3M sucrose, 1 percent PVP-10, 0.005M MES, 50 ppm Casein hydrolysate and 40 ppm Adenine sulfate. Prior to the enzymatic digestions, leaves in the enzyme solution were vacuumed for further enhancement of enzyme infiltration. Incubation of enzymes and leaves took place at 27°–29° C. in the dark or under dim light while sitting on a shaker rotating at a speed of 60–75 rpm. Digestion was completed in 4–6 hours. Prolonged enzyme treatment for up to 16 hours failed to produce any serious damage to protoplasts.

Isolated protoplasts were collected and rinsed in the enzyme solution without the enzymes and PVP-10, by means of centrifugation at a speed of 2,000 rpm for 10 minutes. Harvested protoplasts were counted (using hemocytometer and microscope) and yields estimated. Rinsed protoplasts were soaked in a holding solution to establish an osmotic balance before the protoplasts were removed from the 0.3M rinse solution and cultured in the 0.45M protoplast cultural media. The holding solution was composed of $C_{16}$ as base, to which 0.3M sucrose, 0.15M mannitol, 0.005M MES, 40 ppm adenine sulfate and 50 ppm casein hydrolysate were added.

Protoplasts soaked in the holding solution for 30 to 90 minutes were ready to be cultured. Protoplast cultural media was composed of basically the same ingredients as the holding solution, but 0.25 percent agarose and various concentrations of auxin and cytokinin were added. A concentration ratio of 2 to 1 between 2,4-D and BAP (5 μM 2.4-D and 2.5 μM BAP) in the media and protoplast population densities of 30,000 to 40,000 per ml of media gave better results in protoplast cultures.

Upon culturing, protoplasts should reform the cell-wall in 1 to 2 days. In the following 2 to 3 days, cells start enlarging and getting onset for cell division. On day 6 or 7, the first cell division can be seen. Second, third and advanced cell divisions can follow thereafter. In a period of 12 to 15 days after plating, mini calli of 32 to 128 cells per cluster can be observed by the naked eye and the first transfer of calli onto fresh media for callus proliferation should be done at this stage.

Callus proliferating media contains $C_{16}$ base nutrients, 0.3M sucrose as carbohydrate source, 0.7 percent Agar Nobel as solid base, 0.005M MES as pH buffer and 40 ppm adenine sulfate and 50 ppm casein hydrolysate to promote cell divisions. Hormone free, 2.5 μM BAP with 0.5 μM 2,4-D present in the proliferating media has shown encouraging results. In 7 to 10 days on the proliferating media, calli have grown 2–3 times their original size and turned light green in color.

Using this in vitro system, the following genotypes of Cassava plant (species Manihot esculenta Crantz) have been applied: MCOL 1684; MPAN 12-A; Secundina, CM 489–1; MCOL 22; MCOP 1467; CM 321–188 and MCOL 1940. Results have shown that mesophyll protoplasts isolated from in vitro plantlets of these lines responded positively. Relatively high frequency of mini callus formation in the protoplast cultural media have been constantly obtained.

Advantages of this in vitro system include:
(a) Less time, space and labor are required for in vitro nodal cultures than for growing chamber plants;
(b) Unlike the chamber plants' leaves, in vitro leaf materials are always available and ready for use;
(c) No surface sterilization is needed for in vitro leaves that can avoid the undesirable shocks due to the processes of sterilization done for in vivo leaves;
(d) Shorter periods of time are needed for complete enyzmatic digestion during the protoplast isolating processes for in vitro leaves than for in vivo leaves;
(e) Relatively higher yields of protoplast can be obtained from in vitro materials;
(f) Due to the advantages (c) and (d) mentioned above, more viable protoplasts and high frequency of cell division could be expected when the protoplasts were isolated from in vitro leaves.

Chromosome-doubling attempts through Cassava nodal culture techniques

Colchicine at various amounts has been added to $C_3$ and $C_4$ nodal culture media as a chromosome-doubling agent. Nodal cuttings have been either cultured directly in the media containing colchicine or left in the colchicine media for certain periods of time before being transferred onto normal culture media. As soon as rootings occurred, cytological studies on chromosome staining have been carried out to examine the ploidy level of the plants. Preliminary results have shown that chromosome numbers of colchicine-treated plants are greater than those of the normal diploid plants.

Cassava meristem cultures using $C_3$ and $C_4$ media as basal nutrients $C_3$ and $C_4$ media furnished with 0.5–0.57 μM IAA, 4.5–5 μM BAP, 0.5–0.58 μM GA and 3% sucrose were applied as cultural media. Shoot tips (length 0.5±0.1 mm) were excised and cultured onto the media at 27°–30° C., under 3,000–4,000 lux light with 8 hours dark. Explants grew up to 3 times its original size in 5–7 days and a shoot of about 0.5 cm long established in 10–14 days. In about a month, a 1–2 cm long shoot developed which should be ready for rooting transfer. Hormone-free $C_3$ and $C_4$ with 3% sucrose were determined to be the preferred media for rooting and further shoot development into a plant.

What is claimed is:

1. A hormone free medium for in vitro micropropagation of cassava comprising in parts per million:

| | |
|---|---|
| 1200 | $NH_4NO_3$ |
| 1000–1500 | $KNO_3$ |
| 300 | $MgSO_4.7H_2O$ |
| 150–300 | $NaH_2PO_4.H_2O$ |
| 150–300 | $CaCl_2.2H_2O$ |
| 18.5–37 | $Na_2.EDTA$ |
| 13.9–27.8 | $FeSO_4.7H_2O$ |
| 3.0 | $H_3BO_3$ |
| 10.0 | $MnSO_4.H_2O$ |
| 6.0 | $ZnSO_4.7H_2O$ |
| 0.25 | $Na_2MoO_4.2H_2O$ |
| 0.025 | $CuSO_4.5H_2O$ |
| 0.025 | $CoCl_2.6H_2O$ |
| 0.75 | KI |
| 2.5 | Nicotinic acid |
| 10.0 | Thiamine HCl |
| 1.0 | Pyridoxine HCl |
| 100.0 | M—inositol |
| 0.5 | Glycine |
| 0.5 | Folic acid |
| 0.05 | Biotin |
| 0.5 | D-Ca—Pantothenate |
| 0.25 | Riboflavin |
| 0.5 | Ascorbic acid |
| 0.1 | Choline chloride |
| 1.0 | L-Cysteine HCl |
| 10.0 | Malic acid |
| 50.0 and | Casein Hydrolysate. |

2. A medium according to claim 1 which additionally includes about 3 percent sucrose.

3. A medium according to claim 1 which additionally includes about 3 percent glucose.

4. A method for in vitro micropropagation of cassava comprising cultivating nodal cultures under suitable conditions for growth of cassava cells on a medium comprising in parts per million:

| | |
|---|---|
| 1200 | $NH_4NO_3$ |
| 1000–1500 | $KNO_3$ |
| 300 | $MgSO_4.7H_2O$ |
| 150–300 | $NaH_2PO_4H_2O$ |
| 150–300 | $CaCl_2.2H_2O$ |
| 18.5–37 | $Na_2EDTA$ |
| 13.9–27.8 | $FeSO_4.7H_2O$ |
| 3.0 | $H_3BO_3$ |
| 10.0 | $MnSO_4.H_2O$ |

-continued

| | |
|---|---|
| 6.0 | $ZnSO_4.7H_2O$ |
| 0.25 | $Na_2MoO_4.2H_2O$ |
| 0.025 | $CuSO_4.5H_2O$ |
| 0.025 | $CoCl_2.6H_2O$ |
| 0.75 | KI |
| 2.5 | Nicontic acid |
| 10.0 | Thiamine HCl |
| 1.0 | Pyridoxine HCl |
| 100.0 | M—inositol |
| 0.5 | Glycine |
| 0.5 | Folic acid |
| 0.05 | Biotin |
| 0.5 | D-Ca—Pantothenate |
| 0.25 | Riboflavin |
| 0.5 | Ascorbic acid |
| 0.1 | Choline chloride |
| 1.0 | L-Cystein HCl |
| 10.0 | Malic acid and |
| 50.0 | Casein Hydrolysate. |

* * * * *